United States Patent [19]
Coffey et al.

[11] Patent Number: 5,941,851
[45] Date of Patent: Aug. 24, 1999

[54] PULSED LAVAGE HANDPIECE WITH IMPROVED HANDLE

[75] Inventors: Dennis J. Coffey, Foster; Augustus Felix, Cranston, both of R.I.

[73] Assignee: C.R. Bard, Inc., Murray Hill, N.J.

[21] Appl. No.: 08/679,106

[22] Filed: Jul. 12, 1996

[51] Int. Cl.$^6$ ............................................... A61M 37/00
[52] U.S. Cl. ............................................. 604/131; 604/19
[58] Field of Search .................................. 601/142, 160, 601/161, 162; 604/131, 153, 232, 19

[56] References Cited

U.S. PATENT DOCUMENTS

| | | |
|---|---|---|
| 1,425,152 | 8/1922 | Viers . |
| 2,157,970 | 5/1939 | Rowland et al. . |
| 2,283,778 | 5/1942 | Wilhide . |
| 2,503,226 | 4/1950 | Turner et al. . |
| 2,562,656 | 7/1951 | Blakeslee . |
| 2,564,483 | 8/1951 | Kerr . |
| 3,378,662 | 4/1968 | Sorenson . |
| 3,413,498 | 11/1968 | Bowen . |
| 3,671,699 | 6/1972 | Matthews . |
| 3,676,627 | 7/1972 | Happe . |
| 3,712,970 | 1/1973 | Adie . |
| 3,834,839 | 9/1974 | Krebs et al. . |
| 3,993,054 | 11/1976 | Newman . |
| 4,054,766 | 10/1977 | Kramer . |
| 4,064,447 | 12/1977 | Edgell et al. . |
| 4,108,177 | 8/1978 | Pistor . |
| 4,141,352 | 2/1979 | Ebner et al. . |
| 4,199,344 | 4/1980 | Mumford . |
| 4,256,942 | 3/1981 | Wied . |
| 4,282,867 | 8/1981 | Du Toit ................................. 601/161 |
| 4,328,405 | 5/1982 | Cuneo . |
| 4,351,581 | 9/1982 | Wied . |
| 4,379,214 | 4/1983 | Matthews . |
| 4,405,318 | 9/1983 | Whitney et al. . |
| 4,549,097 | 10/1985 | Ulmer . |
| 4,562,318 | 12/1985 | Sorenson . |
| 4,583,531 | 4/1986 | Mattchen . |
| 4,776,840 | 10/1988 | Freitas et al. . |
| 4,820,889 | 4/1989 | Seghetti . |
| 4,890,340 | 1/1990 | Lovitt . |
| 4,934,494 | 6/1990 | Fushiya et al. . |
| 4,957,193 | 9/1990 | Tamamori . |
| 5,017,747 | 5/1991 | Nagahara et al. . |
| 5,046,486 | 9/1991 | Grulke et al. . |
| 5,097,540 | 3/1992 | Lovitt . |
| 5,140,293 | 8/1992 | Fournier et al. . |
| 5,147,292 | 9/1992 | Kullas et al. ....................... 601/161 X |
| 5,207,697 | 5/1993 | Carusillo et al. . |
| 5,246,367 | 9/1993 | Ito et al. . |
| 5,269,750 | 12/1993 | Grulke et al. . |
| 5,269,762 | 12/1993 | Armbruster et al. . |
| 5,322,511 | 6/1994 | Armbruster et al. . |
| 5,395,312 | 3/1995 | Desai . |
| 5,403,276 | 4/1995 | Schechter et al. . |
| 5,460,604 | 10/1995 | Arnett et al. . |
| 5,464,390 | 11/1995 | Arnett et al. . |
| 5,470,305 | 11/1995 | Arbett et al. ............................ 601/161 |
| 5,470,317 | 11/1995 | Cananzey et al. . |
| 5,484,402 | 1/1996 | Saravia et al. . |
| 5,672,155 | 9/1997 | Riley et al. ............................ 604/154 |
| 5,746,721 | 5/1998 | Pasch et al. ........................... 604/153 |

*Primary Examiner*—Corrine McDermott
*Assistant Examiner*—Cris L. Rodriguez

[57] ABSTRACT

A suction and irrigation handpiece is disclosed having a trigger that cooperates with a locking mechanism to lock the trigger into one a plurality of preselected angular positions. The trigger has a plurality of grooves on an inner surface that removably couple with a tooth of the locking mechanism. The locking mechanism includes a shaft rotatably connected through the housing, a locking arm connected to the shaft, and the tooth at the far end of the shaft. The electrical connections between batteries and a motor in the handpiece also are arranged to facilitate manufacture and uniformly energize the pump at a preset position of the trigger. The handpiece thus has a first conductive lead connected between one pole of the battery and a contact port that is relatively far from the trigger pivot, and a second conductive lead is connected between one port of the motor and the contact port. These two leads form an open circuit at the contact port that may be closed by a conductor connected to the trigger. The other port of the motor is electrically connected to the other pole of the batteries.

11 Claims, 8 Drawing Sheets

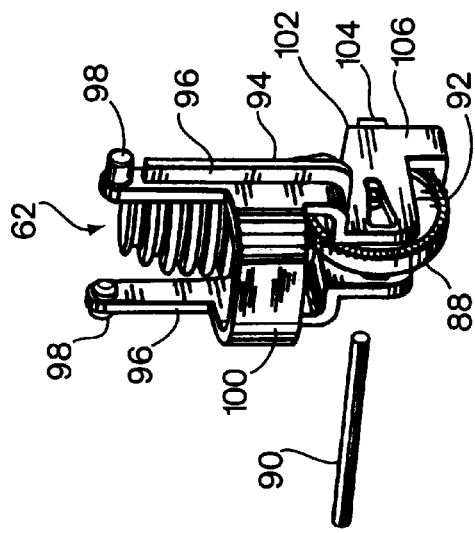
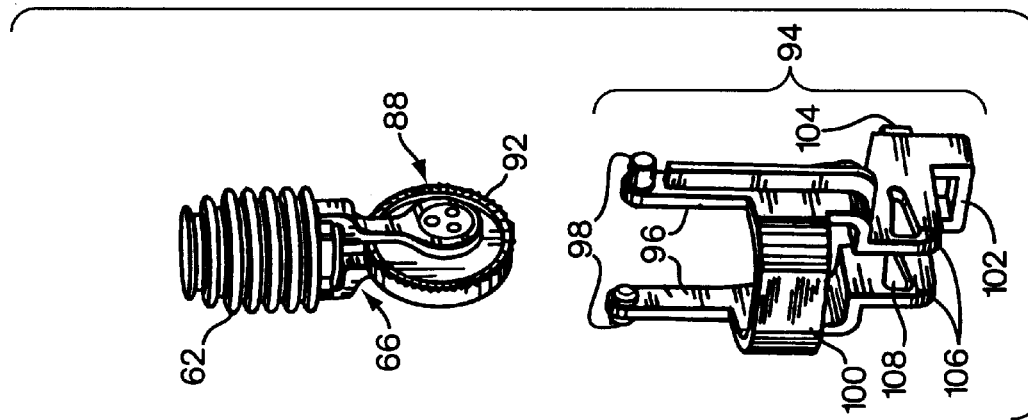
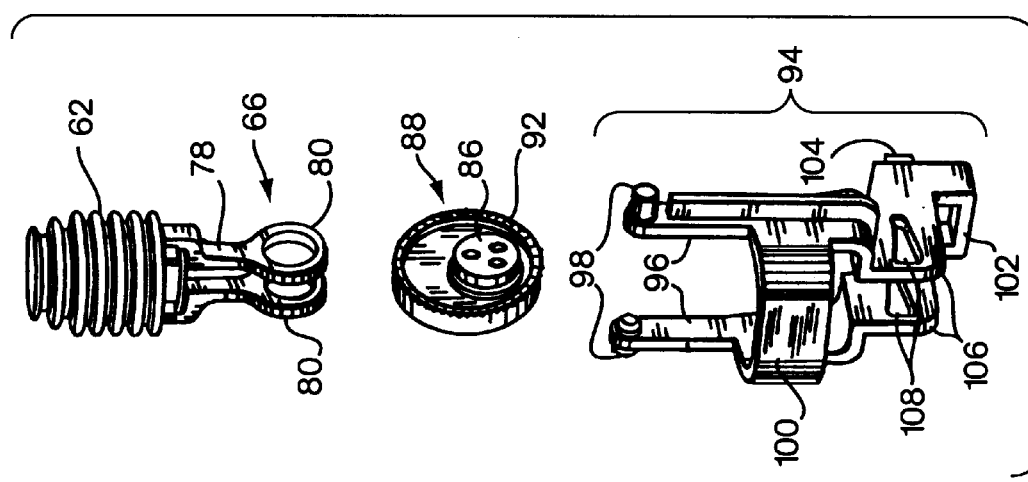
Fig. 5C
Fig. 5B
Fig. 5A

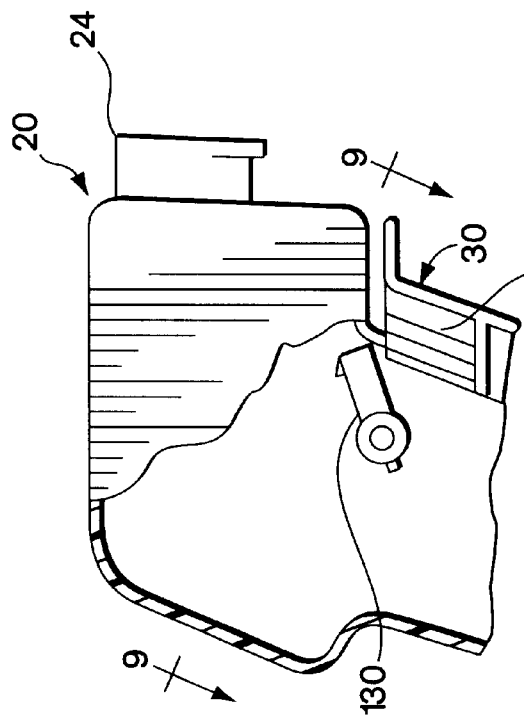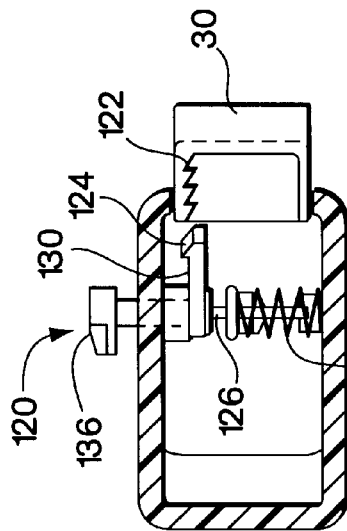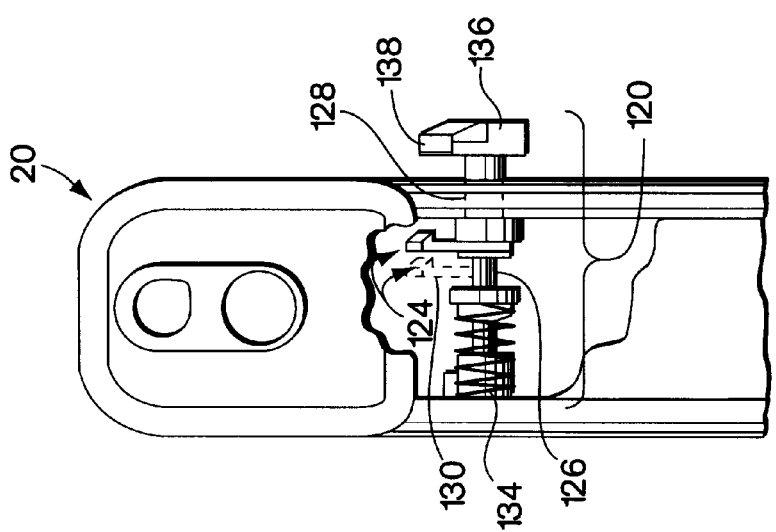

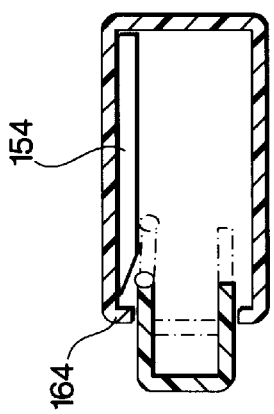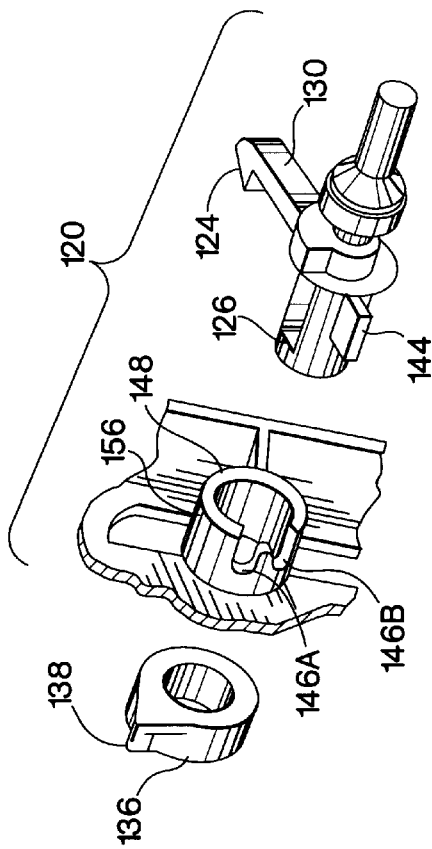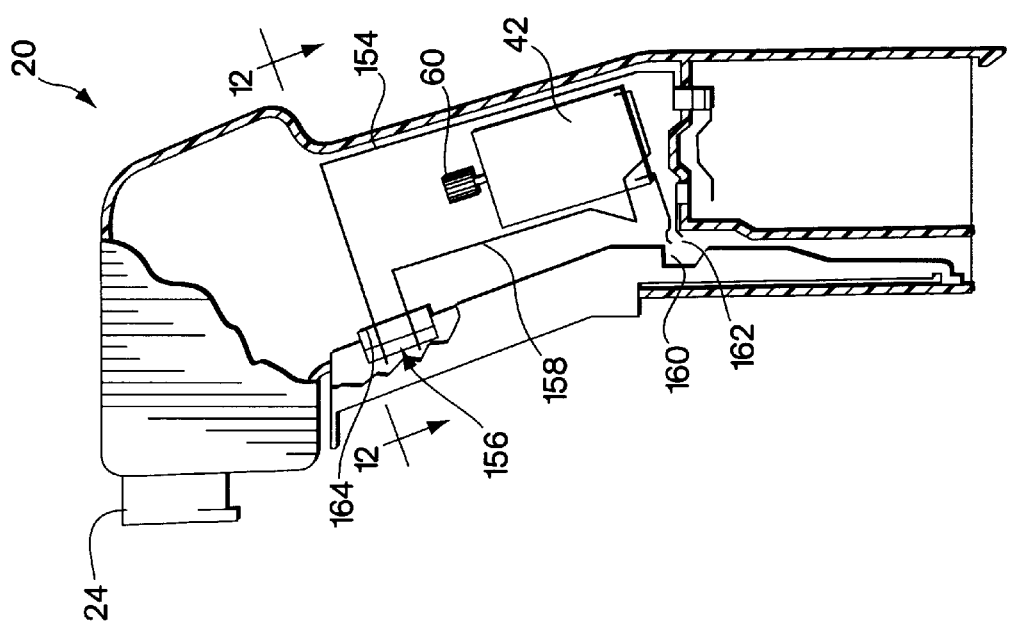

PULSED LAVAGE HANDPIECE WITH IMPROVED HANDLE

FIELD OF THE INVENTION

This invention relates generally to a suction and irrigation device for use in a medical environment, and more particularly relates to a hand-held pulsed lavage handpiece having an improved trigger.

BACKGROUND OF THE INVENTION

During a surgical procedure, it is important to maintain the operative site clean, antiseptic, and free of debris. One common technique for maintaining such a surgical site is to irrigate the site with an irrigation or antiseptic solution. Typically, the irrigation liquid (e.g., saline) is supplied from a reservoir through a tubing to a dispensing handle that is manipulated by a physician, assistant, or attendant. Spent irrigation liquid and other debris that may collect at the irrigation site may be removed by applying a suction to the irrigation site.

A number of combination irrigation and suction devices have been used and proposed. Many deliver irrigation liquid in a pulsatile manner to dislodge debris, and aspirate the site to remove the irrigation liquid and other liquids that collect at the surgical site. One such pump is shown, for example, in co-pending U.S. patent application "Pulsed Lavage Pump with Integral Power Source and Variable Flow Control" to Pasche et al. (Ser. No. 08/389,155, filed Feb. 15, 1995). The Pasche device generally includes a tubing having a first end that is connectible directly to a reservoir, and a handpiece that is connectable directly to the second end of the tubing. All of the components for energizing an internal pump, pumping the irrigation liquid, and controlling the operation of the pump are contained within the handpiece.

Among many other elements, the Pasche handpiece generally includes a housing that contains a variable volume chamber liquid pump, a constant speed D.C. motor to actuate the pump, batteries to energize the motor, and a trigger pivotally mounted to the housing. The trigger acts as a switch between the batteries and motor, and also controls the volume and pressure of irrigation liquid emitted by liquid pump. The pump includes a reciprocating bellows for providing a pulsatile irrigation stream that first draws irrigation liquid from an external reservoir into a valve housing during a filling stroke, and then ejects the liquid from the valve housing during a pumping stroke. The volume and pressure of liquid that is emitted during each pulsing cycle is dependent on the length of stroke effected by the bellows. The trigger controls the stroke of the bellows, and thus the volume and pressure of emitted liquid, by means of a control linkage. As the trigger is depressed inwardly, the control linkage continuously increases the pumping stroke of the bellows, thus increasing the volume and pressure of irrigation liquid emitted by the pump. In order for irrigation liquid to be emitted at a constant volume and pressure, however, the trigger must be maintained in a fixed position. To that end, the pumping system includes an arrangement for locking the trigger in a single fixed position that delivers irrigation liquid at a maximum volume and pressure. This locking arrangement nevertheless does not permit the trigger to be locked in a fixed position that delivers irrigation liquid at constant, non-maximum volumes and pressures. It would thus be desirable to provide an entirely self-contained pulsatile suction and irrigation device that facilitates the delivery of irrigation liquid at one or more preset, non-maximum volumes and pressures.

As noted above, the trigger acts as a switch between the batteries and the motor. To that end, the trigger includes a camming surface near the trigger pivot. When the trigger is depressed inwardly a preselected distance, the camming surface urges a first conductive contact into contact with a second conductive contact to electrically connect the motor to the batteries. This energizes the motor which actuates the pump. Since the stroke of the bellows, and thus the volume and pressure of liquid emitted by the pump, is controlled by the mechanical position of the trigger (i.e. the preselected distance), it is desirable for the preselected distance to be preset during manufacture to a relatively small distance so that first stroke of the bellows is relatively small. This causes the pump to emit liquid at a relatively low pressure and volume, consequently providing the pump with a wider range of pumping volumes and pressures than if the preselected distance is relatively large. During manufacture, however, this preselected distance is difficult to accurately preset because the camming surface is very close to the trigger pivot. According to known leverage principles, even if the trigger is depressed a relatively large distance, the distance that the camming surface may travel still can be very small. A seemingly trivial variation in such a small distance can therefore significantly affect the operation of both the pump and control mechanism. Consequently, two seemingly identical suction and irrigation handpieces having such a contact arrangement undesirably could have different preselected distances. One handpiece therefore could energize with only a slight depression of the trigger (emitting liquid at very low pressures and volumes), while the other handpiece could energize with only a relatively large depression of the trigger (not emitting liquid at very low pressures and volumes). In addition, the first and second contacts can permanently bend due to the forces applied by the camming surface, thus causing the motor to energize at varying, unanticipated positions of the trigger. This undesirably can cause the handpiece to lose a range of operational volumes and pressures for emitted irrigation liquid. It therefore would also be desirable to have a suction and irrigation handpiece that may be more easily manufactured to uniformly energize the pump at a preset position of the trigger.

SUMMARY OF THE INVENTION

In accordance with one aspect of the invention, the trigger in a suction and irrigation handpiece cooperates with a locking mechanism connected through the housing to lock the trigger into one of a plurality of preselected angular positions. This enables the handpiece to deliver irrigation liquid at individual, discrete pulsing volumes and pressures as it limits hand fatigue to a user. To that end, the trigger has a plurality of grooves on an inner surface that removably couple with a tooth of the locking mechanism. The locking mechanism includes a shaft rotatably connected through the housing, a locking arm connected to the shaft, and the tooth at the far end of the locking arm. The shaft is spring biased so that when the shaft is rotated to the proper orientation, the tooth will normally engage the grooves to lock the trigger into one fixed angular position. The tooth may be disengaged from the grooves by forcing the shaft inwardly against the force of the spring, causing the trigger to move outwardly in response to a leaf spring which normally biases the trigger outwardly from the housing. The handpiece also may be used in a continuously variable mode by rotating the shaft so that the tooth does not engage any of the grooves.

In accordance with another aspect of the invention, the electrical connections between the batteries and the motor in the suction and irrigation handpiece are arranged to facilitate manufacture and uniformly energize the pump at a preset position of the trigger. To that end, a first conductive lead is connected between one pole of the battery and a contact port that is relatively far from the trigger pivot, and a second conductive lead is connected between one port of the motor and the contact port. These two leads form an open circuit at the contact port that may be closed by a conductor connected to the trigger. The other port of the motor is electrically connected to the other pole of the batteries. When the trigger is depressed, the conductor connected to the trigger contacts both the first and second leads, thus completing the circuit, energizing the motor and actuating the pump.

It is among the objects of the invention to provide combination suction and irrigation handpiece that facilitates the flow of irrigation liquid from the handpiece at fixed, preset volumes and pressures.

It is another object of the invention to provide a combination suction and irrigation handpiece that may be more easily manufactured to uniformly energize the pump at a preset position of the trigger.

BRIEF DESCRIPTION OF THE DRAWINGS

The foregoing and other objects and advantages of the invention will be appreciated more fully from the following further description thereof, with reference to the accompanying drawings wherein:

FIG. 5A is an exploded view of part of the pump mechanism;

FIG. 5B is an exploded and partially assembled view of the pump components illustrated in FIG. 5A;

FIG. 5C is an illustration of a further stage of assembly of the components of the pump mechanism as shown in FIGS. 5A and 5B;

FIG. 7 is a diagrammatical illustration of a front view of the handpiece, cut away in part, to show the locking mechanism;

FIG. 8 is a diagrammatical illustration of a side view of the handpiece, cut away in part, to show the locking mechanism;

FIG. 9 is a cross-sectional view of FIG. 8 as seen along line 9—9 showing the cooperation between the locking mechanism and the grooves on the trigger;

FIG. 10 is an enlarged view of the locking mechanism and shaft hole from FIG. 4;

FIG. 11 is a diagrammatical illustration of a side view of the handpiece, cut away in part, to show the electrical connections between the motor and the batteries; and FIG. 12 is a cross-sectional view of FIG. 11 as seen along line 12—12 showing the cylindrical conductor at the contact port.

DESCRIPTION OF THE ILLUSTRATIVE EMBODIMENT

Figure 1:
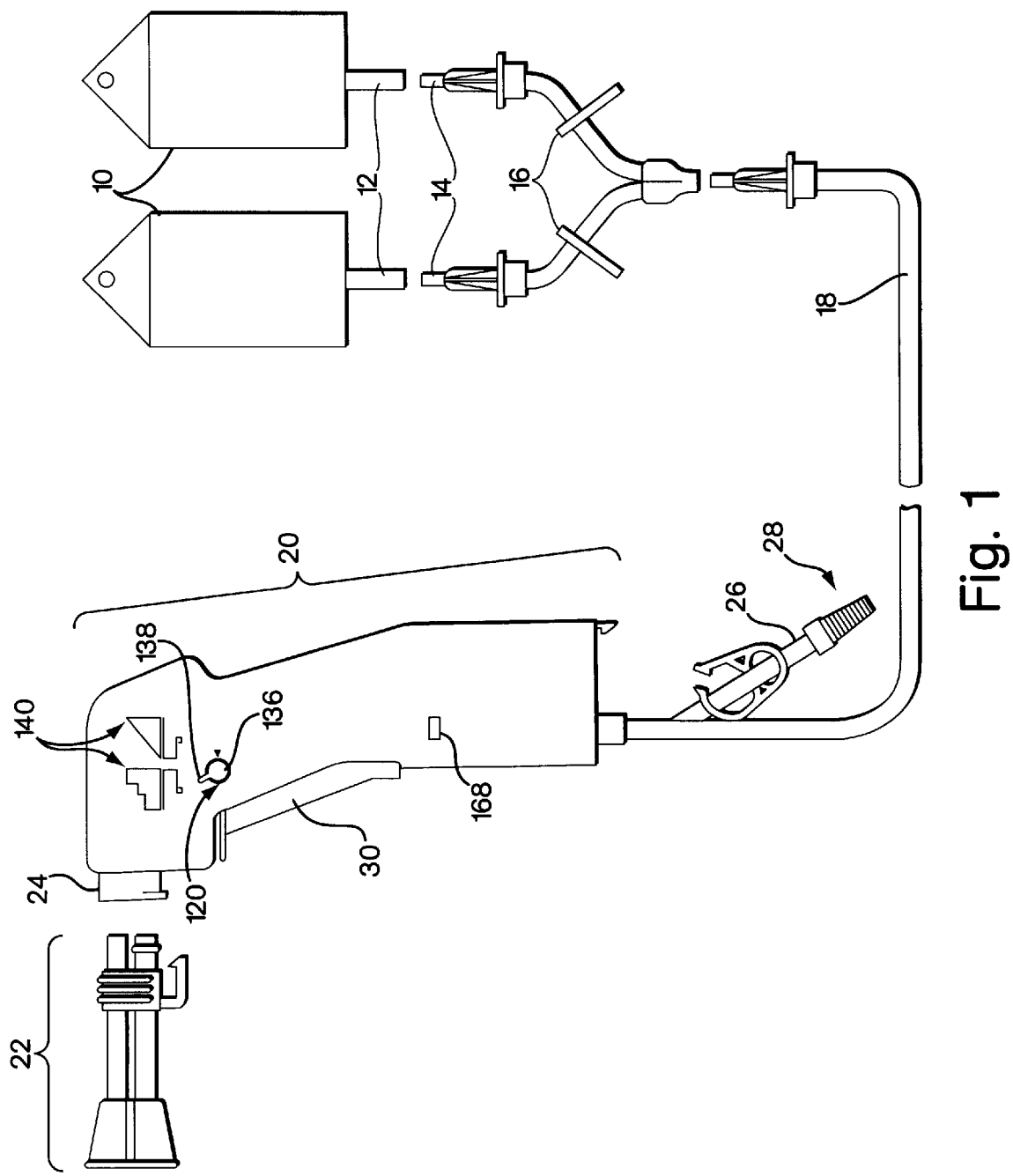
FIG. 1 is a schematic illustration of an irrigation system in accordance with the invention.

As shown in FIG. 1, the irrigation system includes a reservoir of irrigation liquid (e.g., saline), such as one or more bags 10 containing the liquid. The reservoir preferably is adapted to be suspended overhead, as from an I.V. pole, in order to create a gravity pressure head that can facilitate flow of liquid through the system. Each irrigation bag 10 has an outlet port 12 adapted to receive a spike 14 on an end of a flexible tubing to connect the tubing to the irrigation bags 10. Clamps 16 may be provided at various locations along the tubing to control the flow through the tubing. The irrigation system includes a liquid delivery tube 18 that is connectible, at one end, either directly or indirectly, to the irrigation bags 10 and, at the other end, to a handpiece 20.

The handpiece 20 contains the entire pump mechanism, power source and control system for controlling the outlet flow of irrigation liquid from the handpiece 20. The handpiece 20 may be that disclosed in co-pending U.S. patent application "Pulsed Lavage Pump with Integral Power Source and Variable Flow Control" to Pasche et al. (Ser. No. 08/389,155, filed Feb. 15, 1995), the entire disclosure of which being incorporated herein by reference. The handpiece 20 may be somewhat pistol shaped and has a connector socket 24 at its outlet end to which the proximal end of a combined irrigation/suction wand 22 may be detachably connected. Through the socket 24, the wand 22 is connectible to a suction conduit 26 that extends through the handpiece 20, terminating at a suction tube connection 28 that is connectible to a suction source. The handpiece 20 includes a trigger 30 that, when depressed inwardly, closes electrical contacts to initiate operation of a motor 42 that drives the pumping mechanism within the handpiece 20. The pumping mechanism does not operate until the motor 42 is energized. The trigger 30 also is coupled to a control mechanism within the handpiece 20 which controls the volume and pressure which irrigation liquid is emitted from the pumping mechanism. Progressive squeezing of the trigger 30 results in a progressively increased pulsing volume and pressure of irrigation liquid emitted from the pumping mechanism.

Figure 2:
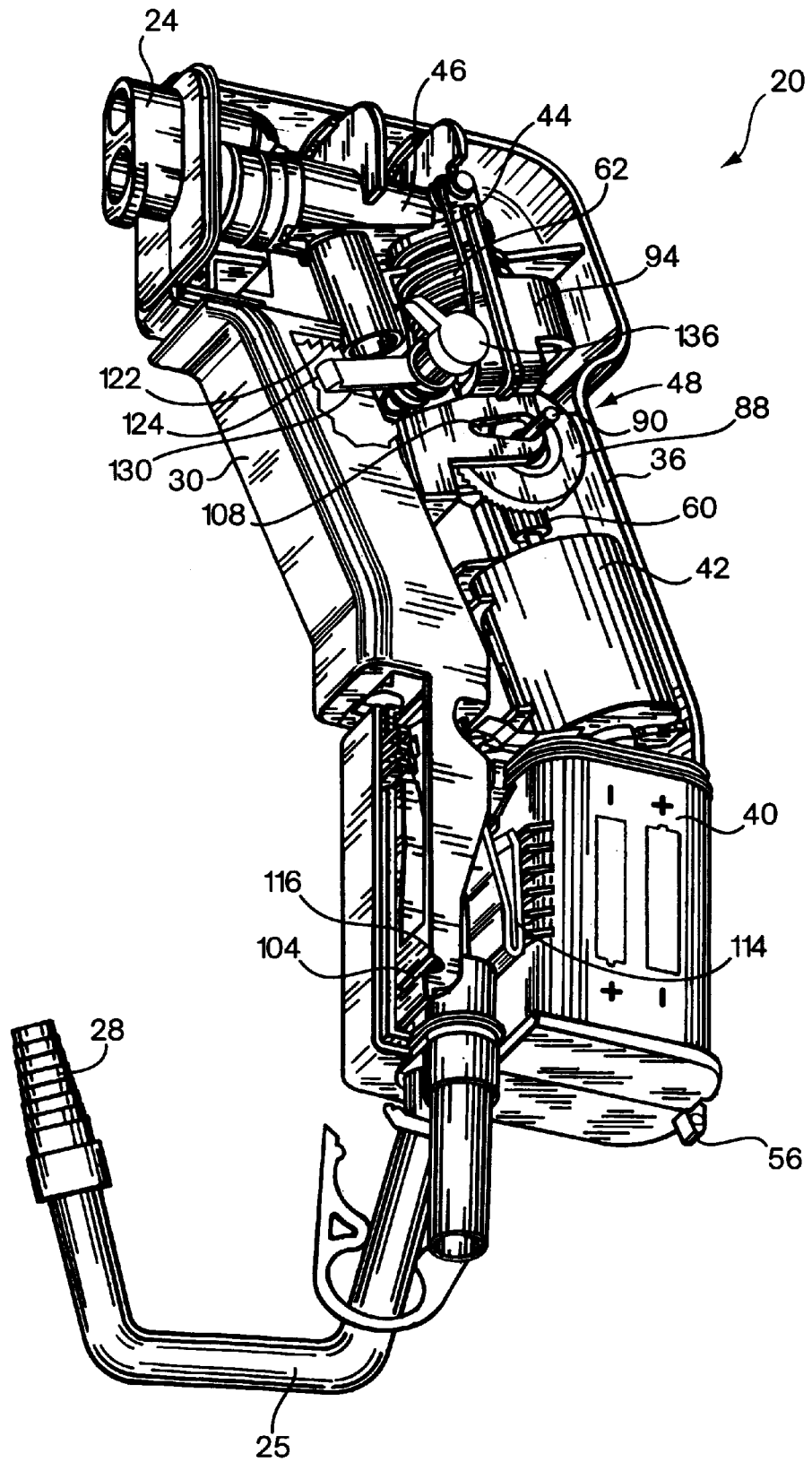
FIG. 2 is an illustration of the handpiece with half of the cover removed to illustrate its interior components.
Figure 3:
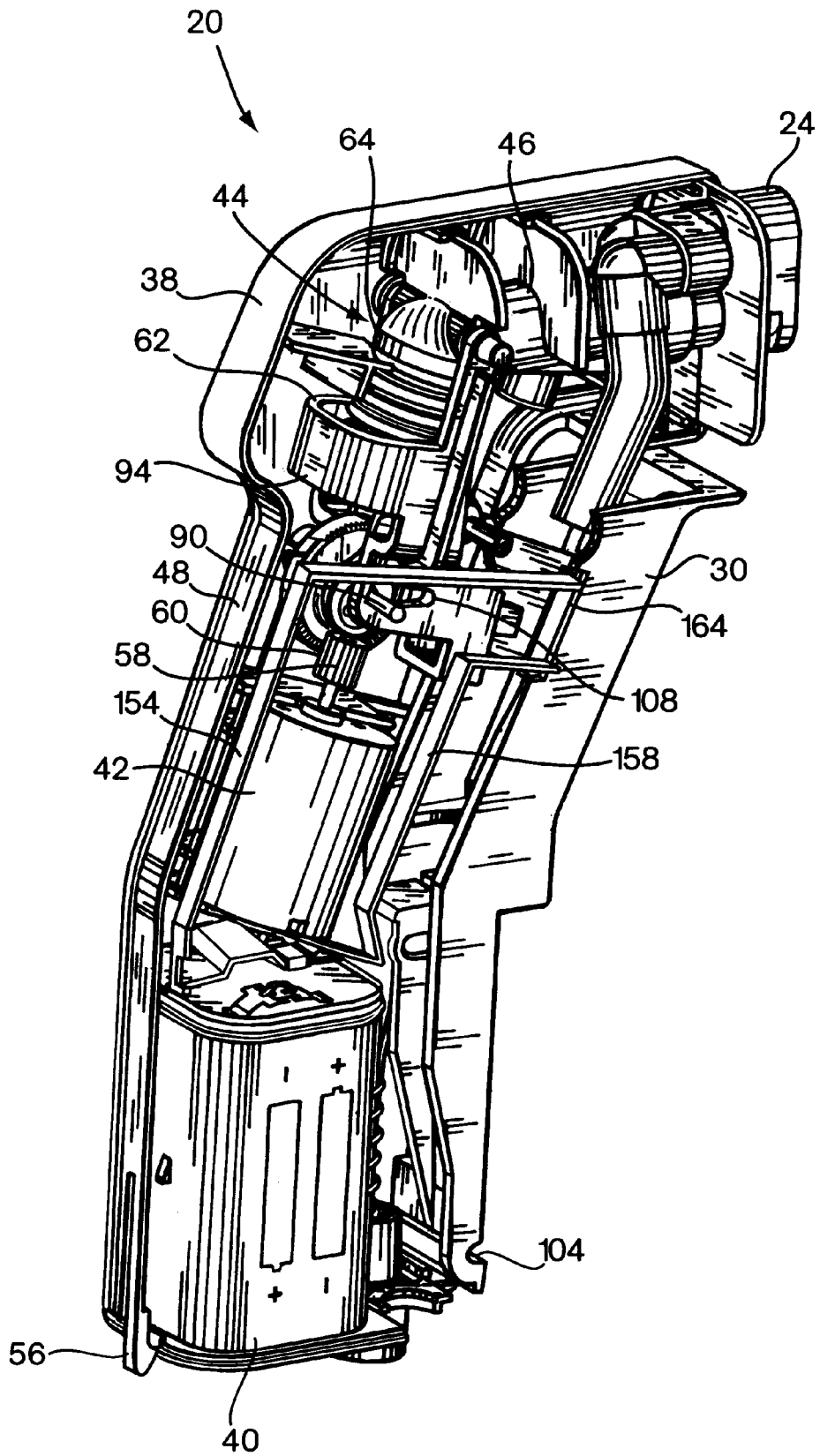
FIG. 3 is an illustration of the handpiece similar to FIG. 2 as seen from the other side of the handpiece and with the cover on the other side removed.
Figure 4:
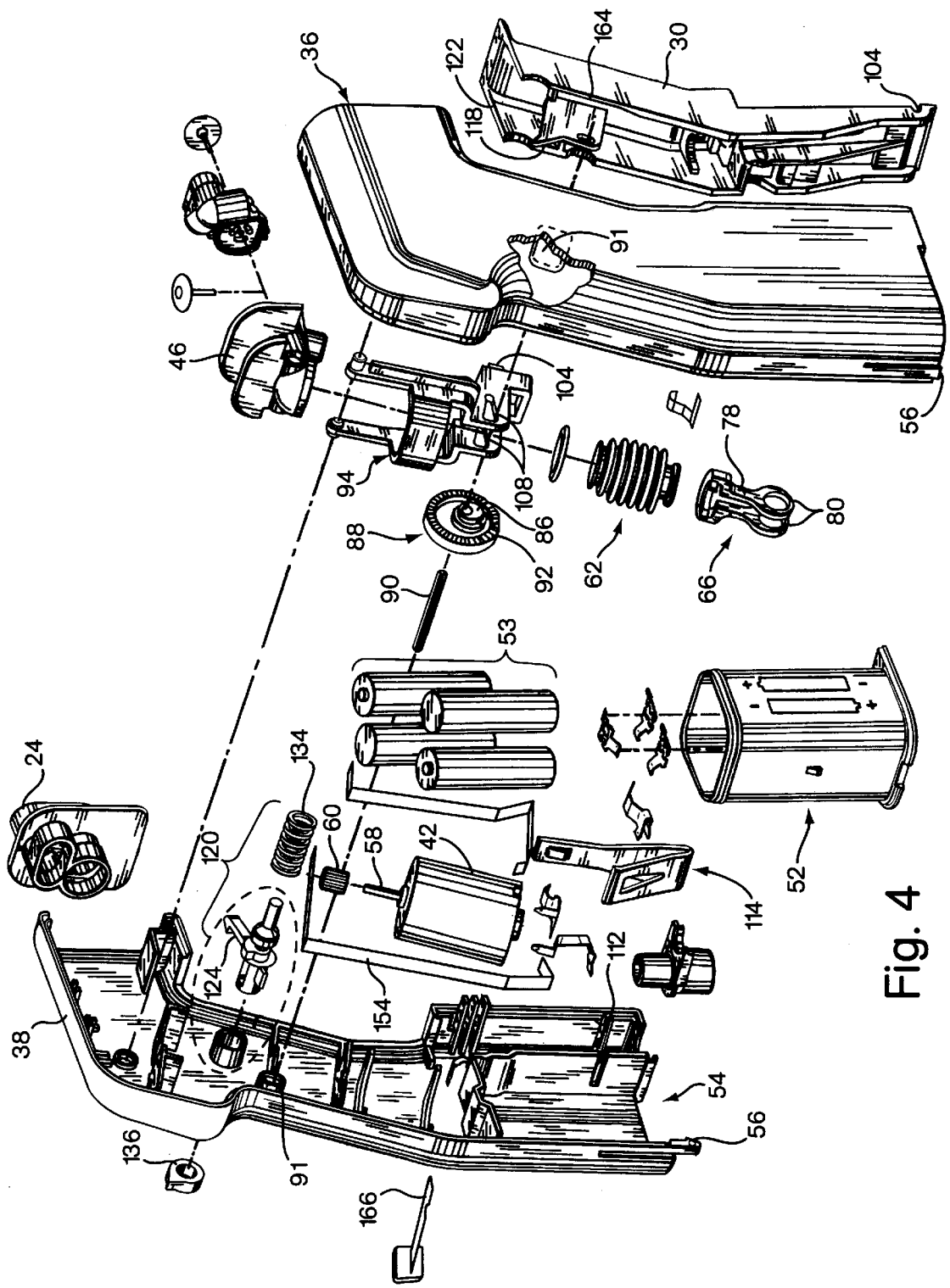
FIG. 4 is an exploded view of the components of the handpiece.

FIGS. 2–4 illustrate the internal assembly of the components of the handpiece 20. The handpiece 20 includes a housing that may be formed from a pair of mateable molded housing sides 36, 38. The interior surface of the housing sides 36, 38, may be formed with various internal projections, walls, sockets and the like to capture securely the internal components as required. Among those components are a battery pack 40, a single speed D.C. motor 42, a bellows pump 44 and associated valve housing 46, and a drive mechanism 48 that operatively connects the motor 42 to the bellows pump 44 to effect a linear reciprocating operation of a bellows 62 within the bellows pump 44. The drive mechanism 48 is controlled by the angular position of the trigger 30, thereby varying the effective pumping stroke of the bellows 62 to control the volume and pressure of irrigation liquid emitted from the handpiece. The trigger 30 also controls an electrical switch (discussed in detail below) that connects and disconnects the battery pack 40 and motor 42. The trigger 30 also may be configured so that when released, the fluid flow line through the handpiece 20 normally is pinched closed to preclude inadvertent leakage of irrigation liquid from the device.

The self-contained battery pack 40 includes a battery case 52 that contains four size AA batteries 53 sufficient to drive the D.C. motor 42. The battery case 52, with loaded batteries 53, is insertable into a receptive socket 54 (FIG. 4) defined within the lower end of the handpiece 20. A flexible latching arrangement may be formed integrally within the housing to secure the battery case 52 in place. The latch mechanism may be constructed to enable the batteries 53 to be removed from the handpiece 20 after the handpiece 20 has been used so that the batteries 53 can be disposed of separately. Electrical contacts (discussed in detail below) are disposed in the handpiece 20 housing to electrically connect the batteries 53 and the motor 42. This normally open electrical connection closes when the trigger 30 is depressed.

The single speed D.C. motor 42 preferably is selected so that it can be adequately powered by four AA batteries 53. The motor 42 includes an output shaft 58 that carries a pinion gear 60. When the motor 42 is operated, the pinion gear 60 drives the drive mechanism 48, as described in further detail below.

The bellows pump 44 itself incorporates a linear reciprocating stroke and preferably is in the form of a flexible bellows 62. The bellows 62 may be formed from any of a variety of materials including a variety of flexible polymers. One end of the bellows 62 is securely attached to a bellows port 64 (FIGS. 6A and 6B) of the valve housing 46. The other end of the bellows 62 is movable and is attached to a reciprocating yoke assembly 66 (FIGS. 5A–5C) that forms part of the drive mechanism 48. As will be described in further detail, the movement of the yoke assembly 66 can be controlled to vary the effective stroke imparted to the bellows 62. The valve housing 46 also includes an inlet port 68 and an outlet port 70, each of which is provided with an umbrella valve, 72,74, respectively. The inlet port 68 is connected to a flexible internal tube (not shown) that connects to the liquid delivery tube 18. The inlet umbrella valve 72 enables liquid to flow from the reservoir through the liquid delivery tube 18 and flexible internal tubing, and then through the inlet umbrella valve 72 into a valve chamber 76. Liquid can flow out of the valve chamber 76 through the outlet umbrella valve 74. As the bellows 62 is reciprocated, the expansion portion of its stroke (i.e. the filling stroke) will cause irrigation liquid to be drawn through the liquid delivery tube 18, the inlet umbrella valve 72 and into the valve chamber 76 and bellows 62. When the stroke of the bellows 62 reverses (i.e. the pumping stroke), irrigation liquid contained within the valve chamber 76 and bellows 62 will be ejected through the outlet port 70, past the umbrella valve 74. Continued reciprocation of the bellows 62 will cause repeated pulsing flow through the system and out through the irrigation/suction wand 22. From the foregoing it will be appreciated that the volume and pressure of liquid that is emitted during each pulsing cycle are dependent on the length of the stroke effected by the bellows 62.

The length of the bellows stroke is controlled by the drive mechanism 48 (including the yoke assembly 66) that, in turn, is controlled by the extent to which the trigger 30 is depressed. As best shown in FIGS. 5A–5C, the yoke assembly 66 includes a pair of parallel connecting arms 78 that each terminate in an integral ring 80. The other end of yoke assembly 66 is connected to the free end of the bellows 62. The rings 80 on the free ends of the connecting arms 78 are rotatably attached to a corresponding pair of circular bosses 86 formed integrally with and on opposite sides of a circular face gear 88. The face gear 88 is mounted on a transverse shaft 90. The transverse shaft 90 extends through the center of the face gear 88, with the bosses 86 being disposed eccentrically to the axis of the transverse shaft 90. The face gear 88 and eccentrically disposed bosses 86 define a crank mechanism. The face gear 88 includes a transversely facing ring of gear teeth 92 that engage and mesh with the teeth on the pinion gear 60 on the motor output shaft 58. The ends of the shaft 90 are rotatably retained in receptive members 91 formed on the inner face of each of the housing halves as described in further detail below. From the foregoing, it will be appreciated that when the motor 42 is driven, the pinion gear 60 drives the face gear 88 and crank mechanism which, in turn, causes the bellows 62 to reciprocate along the bellows axis under the influence of the eccentric crank connection between the yoke assembly 66 and face gear 88.

The transverse shaft 90 is supported in a manner that allows the transverse shaft 90 to have limited freedom of motion in a direction perpendicular to the shaft 90 axis and generally parallel to the axis of the bellows 62. Thus, the ends of the shaft 90 are contained in a pair of parallel rails 91 (FIG. 4) formed on the inner face of each of the housing halves 36 and 38. The ends of the shaft 90 are contained to enable the shaft 90 to move generally parallel to the axis of the bellows 62. The ends of the rails 91 may be enclosed to define somewhat of an oval-shaped entrapment for the ends of the shaft 90. As discussed below, the extent of such shaft 90 movement is governed by the extent to which the trigger 30 is depressed. The extent to which the shaft 90 is permitted to move can vary from no movement up to a predetermined maximum range of movement. When the shaft 90 is retained in its fixed, no movement position, the full amount of the stroke of the yoke assembly 66 will be transmitted to the bellows 62 and, consequently, will effect the maximum amount of pumping permitted by the system. Conversely, when the transverse shaft 90 is released to permit it to move parallel to the bellows axis, the shaft 90 will oscillate within the permitted range of movement. To the extent that the shaft 90 oscillates, that portion of the stroke is not transmitted to the bellows 62, thus reducing the effective stroke of the bellows 62 with a consequent reduction in flow output.

As illustrated best in FIGS. 5A–5C, 6A and 6B, a control member 94 governs the extent to which the shaft 90 is permitted to have limited freedom of movement. The control member 94 may be molded in an appropriate plastic and include a pair of pivot arms 96 having pivots 98 formed integrally at one end. The control member 94 preferably is rigidified by a pair of integral cross members 100 and 102. The cross member 102 also is configured to include a lug 104 adapted to be engaged by the trigger 30 so that when the trigger 30 is squeezed, the control member 94 will pivot in a direction that will progressively restrict the freedom of translational movement of the transverse shaft 90. The pivot arms 96 also include integrally formed control plates 106 that secure the face gear 88 along a plane that is essentially perpendicular to the axis of the shaft 90. To that end, each of the control plates 106 is formed to include an elongated control slot 108. The lengthwise dimension of each slot 108 extends generally perpendicular to the direction of the guide rails 91 to permit translational movement of the shaft 90. The width of each slot 92 diverges from a narrowest end to a wider end, where the width at the wider end may approximate the lengthwise dimension of the rails 91. The control slots 108 are arranged so that the ends of the shaft 90 can protrude through the slots. Thus, the guide rails 91 permit movement of the shaft 90 in a direction generally parallel to the bellows axis and perpendicular to the lengthwise dimension of the slots 108. The extent to which such shaft movement is permitted is controlled by the position of the slots 108 with respect to the shaft 90. When the control member 94 is pivoted to capture the shaft 90 in its most narrow end, the cooperation of the slot 102 and guide rails 91 will maintain the shaft 90 in a fixed position so that the full extent of the reciprocating stroke of the drive mechanism 48 can be transmitted fully to the bellows 62. That configuration is achieved when the trigger 30 is fully depressed. Conversely, when the trigger 30 is released, the control member 94 permits the shaft 90 to move within the wider portion of the control slot 108. In that wider portion, the shaft 90 can oscillate and, to the extent the shaft 90 oscillates, the stroke imparted to the bellows 62 is reduced.

Figure 6A:
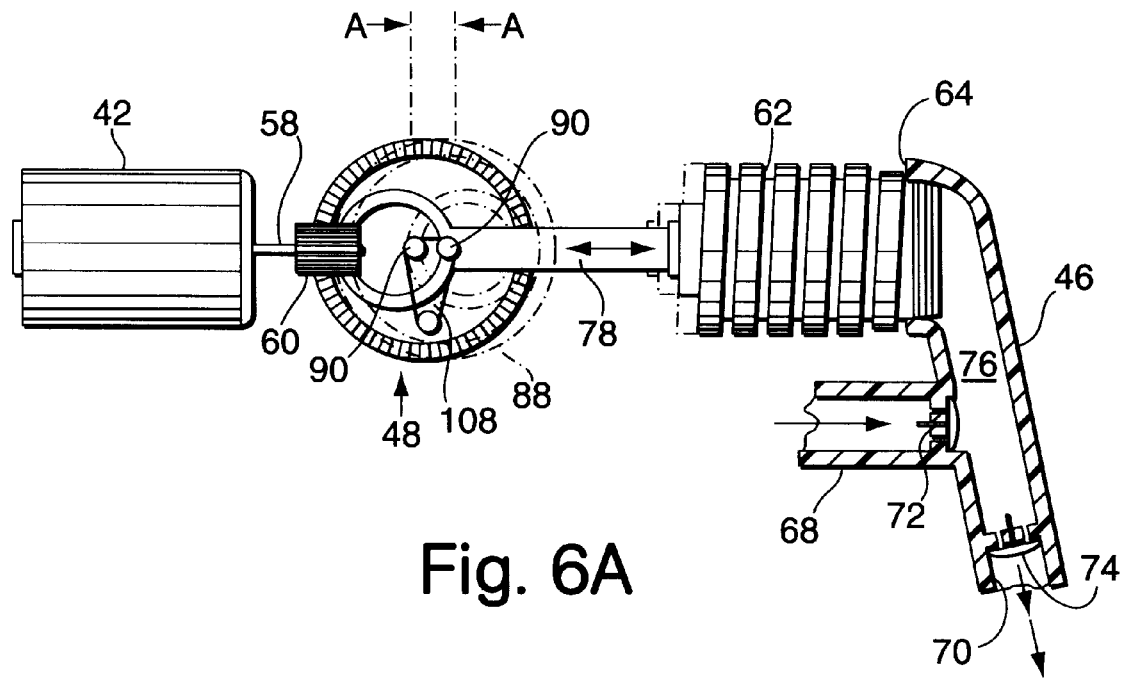
FIG. 6A is a diagrammatic illustration of the mechanism for coupling the motor to the bellows in which the stroke of the bellows is at its minimum.
Figure 6B:
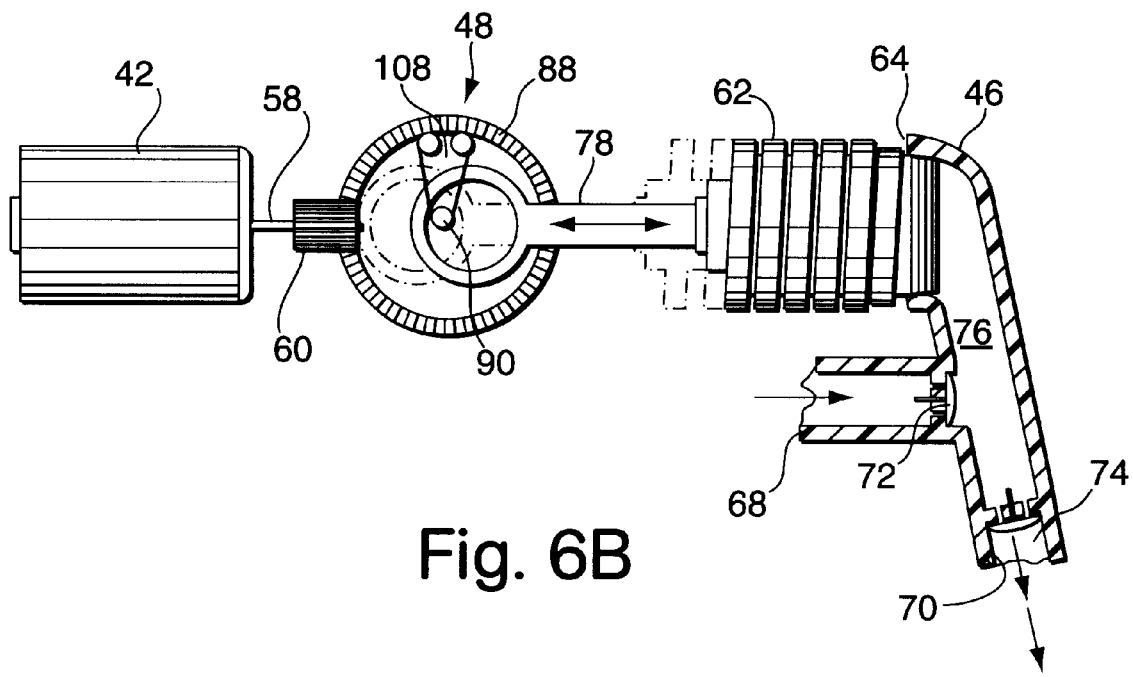
FIG. 6B is an illustration similar to FIG. 7A in which the control mechanism is configured to provide a maximum stroke for the bellows.

FIGS. 6A and 6B illustrate diagrammatically the manner in which the permitted oscillation of the shaft 90 affects the stroke of the bellows 62. In FIG. 6B, the control slot 108 is oriented to capture the shaft 90 and prevent it from oscillatory movement with respect to the housing. Consequently, the face gear 88 is constrained to rotate about a fixed axis and the full extent of the stroke will be transmitted to the bellows 62, as indicated in phantom. In FIG. 6A the control slot 108 is disposed with its widest end in alignment with the shaft 90, thereby permitting a range of freedom of movement, as indicated at A. In this configuration, the amount of the stroke imparted to the bellows 62 is reduced by the dimension A and, as indicated in phantom, the effective stroke of the bellows 62 is reduced. Consequently, the flow rate and output of the device similarly is reduced.

The trigger 30 is mounted for pivotal movement within the housing by engagement of a transverse slot 110 formed in the lower end of the trigger 30 that engages a transverse rib 112 (FIG. 4) formed on the inner surface of the lower front wall of the handpiece 20. The trigger 30 is biased normally in an outward configuration, in which the lower portion of the trigger 30 is urged toward the lower front wall of the handpiece 20. The upper portion of the trigger 30 (which is graspable by the operator) protrudes through an opening defined in the mid to upper region of the front wall. The trigger 30 is biased in this configuration by a leaf spring 114 captured in the lower portion of the housing and bearing against the lower portion of the trigger 30 above a hinge 116. The trigger 30 is connected to the movable end of the control member 94 by an articulated connection between an upstanding inner wall 118 (FIG. 4) on the trigger 30 and the connecting lug 104 that extends from the freely movable portion of the control member 94. The connecting lug 104 and upstanding wall 118 are pinned together by a pin and slot connection, including a slot formed in the upstanding wall 118. Thus, when the trigger 30 is squeezed, the articulated connection between the upstanding wall 118 and the connecting lug 104 will cause the above-described movement of the control member 94 to control the freedom of movement permitted the transverse shaft 90.

In accordance with one aspect of the invention, the trigger 30 cooperates with a locking mechanism 120 to lock the trigger 30 into one of a plurality of preselected angular positions, thus fixing the position of the transverse shaft 90 within the control slots 108. This consequently fixes the amount of oscillatory movement of the shaft 90 within the control slots 108, thus enabling the handpiece 20 to deliver irrigation liquid at individual, discrete pulsing volumes and pressures as it limits hand fatigue to a user. To that end, the trigger 30 has an inner surface that forms one or more grooves 122 (e.g., three) to removably couple with a tooth 124 on the locking mechanism 120. As shown in FIGS. 7–9, the locking mechanism 120 includes a locking shaft 126 rotatably connected through a shaft hole 128 in the housing, a locking arm 130 connected to the locking shaft 126, and the tooth 124 at the far end of the locking arm 130. A coil spring 134 encircles a portion of the locking shaft 126 so that, when the locking shaft 126 is in the proper orientation, the tooth 124 will normally engage the grooves 122 to lock the trigger 30 into one fixed angular position. This fixes the angular position of the trigger 30, relative to the housing, thus causing the bellows pump 44 to emit irrigation liquid at a constant pulsing volume and pressure. The application of an inward force to the locking shaft 126 (against the force of the spring 134) causes the tooth 124 to disengage from the grooves 122, consequently causing the trigger 30 to move outwardly.

The locking mechanism 120 may also include an external knob 136 having a pointer 138 that points to indicia 140 (FIG. 1) on the outside surface of the housing. Accordingly, as shown in FIG. 1, when the pointer 138 is pointing to the indicia 140 on the leftward side of the housing, the trigger 30 is locked in one position as described above (i.e. the "ratchet" mode). Conversely, when the pointer 138 is pointing to the indicia 140 on the rightward side of the housing, the trigger 30 is not locked in one position (i.e., the "continuous" mode). To ensure that the locking shaft 126 is locked in either of the two modes, the locking shaft 126 may include a rib 144 (FIG. 10) that cooperates with notches 146A and 146B formed on an upper rim 148 of a cylindrical wall 150 that encircles the shaft hole 128. The rib 144 on the locking shaft 126 has an edge that slides along the rim 148 to either of the notches 146A or 146B. As the locking shaft 126 is rotated clockwise, for example, the rib 144 slides along the rim 148 until becomes seated in the first notch 146A, thereby preventing the locking shaft 126 from rotating in any direction. The rib 144 may be unseated and rotated from engagement with the first notch 146A by first applying an inward force to the locking shaft 126, and then rotating the locking shaft 126 in a counterclockwise direction. As the locking shaft 126 is rotated counterclockwise, the rib 144 similarly slides along the rim 148 until it becomes seated in the second notch 146B, similarly preventing the locking shaft 126 from rotating in any direction. Similar to when the rib 144 is in the first notch 146A, the rib 144 may be disengaged from the second notch 146B by first applying an inward force to the locking shaft 126, and then rotating the locking shaft 126 in a clockwise direction.

In accordance with another aspect of the invention, the electrical connections between the batteries 53 and the motor 42 are arranged to facilitate manufacture and uniformly energize the bellows pump 44 at a preset position of the trigger 30. To that end, as best shown in FIGS. 11 and 12, a first conductive lead 154 is connected between one pole of the battery pack 40 and a contact port 156 that is relatively far from the trigger pivot, a second conductive lead 158 is connected between one port of the motor 42 and the contact port 156, and a first leaf conductor 160 connected to the other motor port is normally biased against a second leaf conductor 162 connected to the other battery pole. The two leads 154 and 158 form an open circuit at the contact port 156 that may be closed by a cylindrical conductor 164 connected to the trigger 30. When the trigger 30 is depressed a preselected distance, the cylindrical conductor 164 connected to the trigger 30 contacts both the first and second leads 154 and 158, thus completing the circuit and energizing the motor 42. The ends of the first and second leads 154 and 158 at the contact port 156 may be tapered (FIG. 12) so that the cylindrical conductor 164 can slide easily upon the leads 154 and 158. Since the cylindrical conductor 164 is relatively far from the trigger pivot, the preselected distance may be easily set during manufacture. Similarly, since the preselected distance may be set to be relatively small, the handpiece 20 may emit irrigation liquid at a wider range of pulsing volumes and pressures. In addition, the reliability of the handpiece 20 is improved over prior art designs since no leads need to be bent by a camming surface.

The handpiece 20 also may be configured to prevent the motor 42 from inadvertently energizing. To that end, a locking pin 166 (FIG. 4) is provided that is inserted through the device through a lock pin hole 168 (FIG. 1) formed in the side of the housing (FIG. 4). When inserted, the lock pin 166 is positioned between the two leaf contacts 160 and 162 (FIG. 11 shows the leaf contacts) to prevent any electrical communication between the two contacts 160 and 162. Accordingly, although the two leaf contacts 160 and 162 are normally maintained closed, the locking pin 166, which is formed from a non-conductive material (e.g., plastic), prevents inadvertent operation of the motor 42 and depletion of the batteries 53.

From the foregoing it will be appreciated that the invention provides an improved pulsing irrigation device for use in surgical and other medical environments where pulsed lavage is desirable. The system is extremely simple in operation and set up, may be more easily manufactured to uniformly energize the bellows pump 44 at a preset position of the trigger 30, and facilitates the flow of irrigation fluid at discrete, preset pulsing volumes and pressures.

It should be understood, however, that the foregoing description of the invention is intended merely to be illustrative thereof and that other embodiments and modifications may be apparent to those skilled in the art without departing from its spirit.

Having thus described the invention what we desire to claim and secure by Letters Patent is:

1. A hand-held suction irrigation device comprising:

a housing;

a motor within the housing;

a battery within the housing to energize the motor;

a plurality of leads extending from the motor and the battery, the leads forming a normally open circuit between the motor and battery at a contact port, the leads including a first conductor extending between at least one terminal of the battery and the contact port and the second conductor extending between at least one terminal of the motor and the contact port;

the first conductor further including a first leaf spring contact extending from at least one of the positive or negative terminals of the battery;

the second conductor including a second leaf spring contact extending from at least one of the terminals of the motor;

the first leaf spring contact being normally biased against the second leaf spring contact;

a trigger movably connected to the housing, the trigger having an electrically conductive contact that slides across the plurality of leads and selectively closes the open circuit, at the contact port, to energize the motor;

an aperture formed by the housing; and a pin removably extending through the aperture, the pin preventing electrical contact between the first leaf spring contact and the second leaf contact.

2. A hand-held suction irrigation device comprising:

a housing;

a trigger mounted to the housing for movement about a pivot;

a motor within the housing;

a battery within the housing to energize the motor;

a fluid pump contained with the housing;

a mechanical drive train coupling the motor and the fluid pump, the drive train enabling the output of the fluid pump to be varied as a function of the degree of trigger movement, thereby varying the output flow from the surgical irrigation device;

the trigger being mechanically connected to the drive train to effect such variation in output;

a plurality of leads extending from the motor and the battery, the leads forming a normally open circuit between the motor and battery at a contact port that is spaced substantially from the pivot;

the trigger having a contact spaced substantially from the pivot and located so that as the trigger is moved about the pivot the contact will close the normally open circuit at the contact port, whereby the contact and open circuit leads can be located to initiate operation of the motor when the trigger and mechanical drive train are in a predetermined relation;

a groove formed on a surface of the trigger that is exposed internally with the housing;

a lock movably mounted to the housing the lock having a locking member disposed within the housing for movement between positions in which the locking member is selectively engaged or disengaged with the groove.

3. The hand-held suction irrigation pump device as defined by claim 2 wherein the lock further comprises:

a shaft extending through the hole in the housing;

the locking member comprising an arm connected to the shaft at a first end and terminating at a tooth at a second end;

the tooth being aligned to removably couple with the groove.

4. The hand-held suction irrigation device as defined by claim 2 further comprising three grooves formed on the internal surface of the trigger.

5. A hand-held suction irrigation device comprising:

a housing;

a trigger movably connected to the housing, the trigger having an internal surface which defines a groove;

a liquid pump contained within the housing and being controllable by the movement of the trigger;

a hole formed in the housing; and a lock rotatably fastened through the hole, the lock having a locking arm that is aligned to removably couple with the groove on the internal surface of the trigger;

the lock further comprising:

a shaft extending through the hole in the housing;

the locking arm being connected to the shaft at a first end and terminating at a tooth at a second end;

the tooth being aligned to removably couple with the groove.

6. The hand-held suction irrigation device as defined by claim 5 wherein the lock further comprises a spring circumscribing the shaft.

7. The hand-held suction irrigation device as defined by claim 5 further including a wall circumscribing the hole on an interior surface of the housing, the wall having a rim that forms a depression.

8. The hand-held suction irrigation device as defined by claim 7 wherein the shaft includes a rib that slides along the rim of the wall, the rib cooperating with the depression to control the longitudinal motion of the shaft.

9. The hand-held suction irrigation device as defined by claim 5 wherein the trigger includes three grooves.

10. The hand-held suction irrigation device as defined by claim 5 wherein the lock includes a knob having a pointer and the housing includes indicia upon the outer surface of the housing, the pointer pointing to indicia to indicate whether the lock is coupled to the groove.

11. The hand-held suction irrigation device as defined by claim 5 further including:

a motor within the housing;

a battery within the housing to energize the motor; and a plurality of leads extending from the motor and the battery, the leads forming a normally open circuit between the motor and battery at a contact port;

the trigger having a contact that selectively closes the open circuit, at the contact port, to energize the motor.

* * * * *